United States Patent [19]

Strong et al.

[11] Patent Number: 5,572,115
[45] Date of Patent: *Nov. 5, 1996

[54] DEVICE AND METHOD FOR MEASURING CHARGE CARRYING ACTIVITY IN GENERALLY NON-CONDUCTIVE MATERIALS

[75] Inventors: A. Brent Strong, Sandy; R. Scott Merrell, Provo; Barry M. Lunt, Orem, all of Utah

[73] Assignee: Brigham Young University, Provo, Utah

[ * ] Notice: The term of this patent shall not extend beyond the expiration date of Pat. No. 5,432,435.

[21] Appl. No.: 315,267

[22] Filed: Sep. 29, 1994

Related U.S. Application Data

[63] Continuation-in-part of Ser. No. 948,008, Sep. 22, 1992, Pat. No. 5,432,435.

[51] Int. Cl.⁶ ............................ G01N 27/02; G01R 27/02
[52] U.S. Cl. ............................ 324/71.1; 324/693; 324/705
[58] Field of Search ...................... 324/71.1, 691, 324/693, 705, 706, 714, 723

[56] References Cited

U.S. PATENT DOCUMENTS

| | | |
|---|---|---|
| 3,791,792 | 2/1974 | Lindsay . |
| 3,935,053 | 1/1976 | Armstrong, Jr. . |
| 4,129,824 | 12/1978 | Howes . |
| 4,710,550 | 12/1987 | Kranbuehl . |
| 4,777,431 | 10/1988 | Day et al. . |
| 4,891,591 | 1/1990 | Johnston et al. . |
| 5,089,780 | 2/1992 | Megerle . |
| 5,095,278 | 3/1992 | Hendrick . |
| 5,184,077 | 2/1993 | Day et al. . |
| 5,200,027 | 4/1993 | Lee et al. . |
| 5,210,449 | 5/1993 | Walsh . |
| 5,432,435 | 7/1995 | Strong et al. ........................ 324/705 |

OTHER PUBLICATIONS

In–Process Controlled Curing of Resin Matrix Composites by Michael J. Yokota Date Unavail.
Dielectric Analysis of Thermoset Cure by Stephen D. Senturia and Norman F. Sheppard, Jr., 1986.

Primary Examiner—Kenneth A. Wieder
Assistant Examiner—Glenn W. Brown
Attorney, Agent, or Firm—Thorpe, North & Western, L.L.P.

[57] ABSTRACT

A method for detecting extent of cross-linking of a high impedance material during a shelf life, slow state transition or during use, the method including: applying a test signal through a sensor to the material and through a reference material; determining a voltage difference between the test signal applied to the material and the reference material as the reference voltage; and correlating the voltage difference as a relative indicator of the extent of chemical change which has occurred within the material. Also disclosed is a device for implementing the subject method.

33 Claims, 5 Drawing Sheets

DEVICE AND METHOD FOR MEASURING CHARGE CARRYING ACTIVITY IN GENERALLY NON-CONDUCTIVE MATERIALS

CONTINUATION-IN-PART APPLICATION

The present application is a continuation in part application of U.S. application Ser. No. 07/948,008, filed Sep. 22, 1992, now U.S. Pat. No. 5,432,435.

BACKGROUND OF THE INVENTION

1. Field of the Invention

This invention relates to a process for determining the charge carrying activity, in generally non-conductive, materials such as paint, dental resin, B-staged resin, concrete, dielectric fluids, food, etc. More particularly, the present invention pertains to the detection of changes in charge carrying activity of nearly any non-conductive/semi-liquid material, so as to enable a user to determine the extent of chemical change, and thus the amount of curing (paints, adhesives and long chain polymers), remaining useful life (dielectric fluids) or other conditions of a given material during times other than rapid state transitions.

2. Prior Art

The detection of cross-linking in low-conductive polymeric materials became common place in the thermosetting resin industry to determine when thermosetting resins are properly cured. These resins form a class of very useful plastics which have been applied throughout the aerospace industry, construction industry, automotive manufacturing, medical applications, adhesives, and in virtually every area where permanent characteristics of weatherability, structural stiffness, strength and ease of manufacture through molding process provides an advantage over competing metals, ceramics and other compositions. Dental applications include filling and facia materials which are applied to the tooth in liquid form and then polymerized by UV radiation or other known techniques. Many paint compositions are a form of thermosetting resin whose application depends on having a uniform liquid state which can be readily applied by brush or air gun. Matched die, filament winding, transfer molding, lay up molding and pultrusion techniques for fabricating structural and component parts, housings, etc., depend on maintenance of a flowable condition which can wet fibers or quickly fill mold cavities in a liquid state.

Tests for determining cross-linking within the resins were developed to test when the resins had properly cured, i.e. passed through a state transition from a flowable resin to a thermoset solid. These resin materials are typically manufactured in a low viscous liquid state wherein the polymer material has incurred minimal cross-linking prior to the curing stage. It is, of course, this cross-linking that causes the state transition by solidifying the thermosetting composition into a permanent, rigid structure characterizing this group of plastics. The cross-linking of the polymers typically occurs under high heat, which is commonly referred to as the curing stage.

There is increasing interest in the composites industry to monitor, adjust and optimize the cure cycle of thermoset polymers. Accordingly, it is known to evaluate cross-linking during actual cure using viscometers, infrared meters, and microdielectrometers. This period of evaluation is characterized by the resins being subjected to high temperatures used to fully complete the curing of the materials. The primary interest in rapid state transition is to identify the gelation point and then to confirm final stage at which the curing process is complete, so that the final product can be removed without extending cure time and conditions beyond that which is necessary. This enables efficient use of expensive equipment and also insures that the manufactured part is not removed from the mold prior to complete cross-linking.

While measuring the cross-linking within the thermosetting resin is important during the curing stage, it is also important to determine the amount of cross-linking which has occurred in the pre-cure stage, i.e. the time between manufacture of the resin and the time at which the resin is cured. During this period which is often referred to as the shelf life of the product, the resin under goes a very slow transition from one state to another via the cross-linking of polymers. However, until the present invention, those skilled in the art believed that the measurement of generally non-conductive liquids and semi-liquids (i.e. during the shelf life or slow state transition stage) if possible, would be impractical and expensive at the ambient or low temperatures at which the liquids are maintained to prevent cross-linking.

The amount of curing which occurs while the product remains unused is important to know because premature curing results in a permanent, irreversible condition which makes the material useless for further processing. Indeed, the extent of waste arising because of premature curing of thermosetting materials is substantial. In industries where partially cured materials must be discarded for safety reasons, the losses are even more significant. For example, the manufacture of high performance aircraft components from resins that have already partly cured could result in weakened structures that put lives in jeopardy. Therefore, it is very likely that a substantial amount of good resin is discarded because of suspicion of excessive pre-cure.

Because most resins will inherently begin cross-linking upon manufacture and will continue such cross-linking until finally cured, measures are taken to reduce and control this process. The primary control measure is to maintain the resins at low temperatures to reduce reaction rates to a minimum. This low temperature environment needs to be maintained until the material is ready for final curing. Unfortunately, the resin material appearance does not always reflect the degree of curing which has occurred during this slow state transition (pre-cure) stage. If variations in temperature occur during storage, their impact may be substantially unknown. The low temperatures at which the resins, etc, are kept have also been a major factor in discouraging the use of cross-linking analysis to determine the extent of slow state transition, because most of those skilled in the art believed that a low temperature resin liquid would not provide sufficient indicators of cross-linking, or that the indicators would be hidden in background noise.

With paints and adhesives, viscosity provides a useful measure of acceptability of slow state transition (pre-cure) cross-linking. In general, their shelf life is determined by the time required for the material to set up or become too viscous to flow well. There are, however, no current tests to determine the actual state of cross-linking in paints and adhesives. Current practice is to examine the viscosity of the materials qualitatively as noted, or perform sample tests to determine the performance of these resins in a particular application.

With respect to polymers used in a matrix material for fiber reinforced composites, there are two distinct time periods during which cross-linking takes place. The first period can be called the shelf life of the material and the second is the curing cycle. Users of fiber reinforced thermosetting composites have created several mechanical tests to evaluate the state of cumulative cross-linking in the slow state transition (pre-cure) stages. For example, tack and drape properties give an indication of the extent of cure. These tests are acknowledged to be highly subjective and unreliable, and are at best general qualitative indicators having little quantitative value.

A more specific application of thermosetting resins for composite materials is to impregnate a layer of fiber reinforcement with resin, and then store this "pre-preg" or "B-staged" material for later use. Obviously, this B-staged material will have a limited shelf life, depending upon the rate of continued cross-linking, which is affected mainly by temperature. It is presently difficult, subjective, and consumptive of material to test the B-staged material for the extent of cross-linking. If the B-staged material has reached a particular stage of cross-linkage, it is no longer usable material and must be discarded on the basis of storage time, rather than on the actual amount of cross linking.

Providing a device and method which enables users to derive information about cross-linking during the slow state transition (shelf life) allows repeated measurement of resins, adhesive, paints and the like, to minimize waste and product failure.

Thus, there is needed an effective device and method for measuring low-conductivity or nonconductive materials repeatedly to determine the extent of cross-polymerization during the shelf-life or slow state transition period, etc., to enable more effective determination of the conditions of materials. Such a device and method could provide quantitative determination of which materials should be discarded and which can be safely or effectively used for their intended purpose.

OBJECTS AND SUMMARY OF THE INVENTION

It is an object of the present invention to provide a device and method for enabling the determination of the extent of cross-linking in any resistive polymer.

It is yet another object of this invention to provide a device and method as stated above which can be effectively applied during the pre-cure/shelf life/slow state transition stage of material, wherein the material is maintained at low temperatures for minimizing cross-linking.

A further object of the present invention is to provide a device and method for providing ongoing or continuous detection of charge carrying activity within a material, which can be applied to paints, adhesives, caulking, dental resins, resins for composites, concrete, food and other low-conductive or nonconductive fluids.

Yet another object of this invention is to provide the objects noted above within a low cost device which is convenient to use under virtually all situations.

These and other objects are realized in a method for detecting extent of chemical change of a high impedance material. This method includes the steps of:

a) applying a test signal through a sensor to the polymer material in a slow state transition stage to determine a level of impedance and corresponding sample voltage representative of a degree of chemical/physical change within the material;

b) applying the same test signal through the sensor to a reference material having a fixed resistance to determine a reference voltage;

c) determining a difference between the test signal applied to the polymer at slow state transition stage and the test signal applied to the reference material as the reference voltage; and d) correlating the voltage difference as a relative indicator of the extent of chemical/physical change which has occurred within the polymer material, based on comparison of magnitude of the voltage difference with respect to a comparable potential range of impedance for the polymer material from its lower impedance stage to its high impedance stage.

Another aspect of this invention is represented by a device for testing extent of charge carrying activity of a material in a slow state transition stage, wherein the device comprises a signal generator capable of generating a low frequency, low amplitude signal with an attached sensor adapted for receiving a quantity of the material to be tested, wherein the sensor has a known impedance. A reference material is provided which has a resistance approximately equal to a known impedance of the material at a predetermined extent of chemical and/or physical change. The device includes voltage means for determining voltage difference between a signal detected through the sensor with polymer material and a signal detected through the sensor at the reference material. Means are provided and coupled to the voltage means for converting the voltage difference to a factor representing the extent of chemical and/or physical change which has occurred within the material.

Other objects and features of the present invention will become apparent to those skilled in the art, based upon the following detailed description of a preferred embodiment, taken in combination with the accompanying drawings, and several examples of the preferred embodiment used to determine impedance in different materials to determine the condition of the materials due to their charge carrying activity.

DETAILED DESCRIPTION OF THE INVENTION

Figure 1:
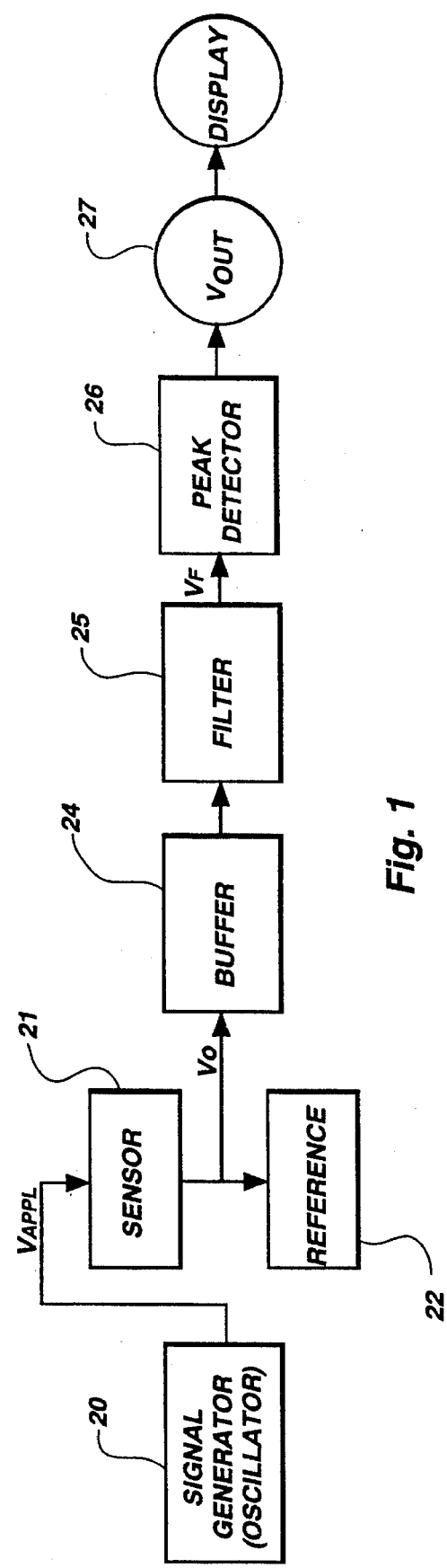
FIG. 1 shows a graphic, block diagram of the various functional features of the present invention.

The present inventors have discovered that it is possible to determine the extent of cross-linking in any resistive material, even during the pre-cure/shelf life/slow state transition stage of the material. Specifically, the invention comprises a method for detecting the extent of chemical change of a high impedance material during a the slow state transition stage commonly referred to as the shelf life or pre-cure stage (for polymers) of the article. As will be appreciated by those skilled in the art, the dominant characteristics of a product change very slowly over this time period, and prior to the present invention, such changes were considered to be impractical, if not impossible, to detect by measuring impedance of the material. Rather, impedance was used during rapid state transition, commonly referred to in the thermosetting resin industry as the cure stage or curing stage in which high heat or other types of energy are applied to the resin to form the hardened material.

The first step of this method, when used for analyzing polymer materials, involves applying a test signal through a sensor to the polymer material in the slow state transition stage to determine a level of impedance and corresponding sample voltage representative of a degree of cross-linking within the material. Typically, this signal will be an electric current whose amplitude is inversely proportional with the resistance of the polymer in accordance with Ohms law I=E/R. Other techniques of measuring the resistance of the material may likewise be employed.

The test signal is conducted directly into the polymer by means of an interdigitated electrode sensor which is inserted in contact with the polymer. Other than the interdigitated relationship of the electrodes, the geometry of the probe is not significant. Any conductive material coupled at one end to a voltage source may be used as a probe. Where the sensor is used with high resistivity resins or other high resistivity polymers, the probe should be shielded by a shielding means coupled around the sensor to shield from static electricity. The shield is typically made of copper, but can be made of aluminum, nickel, steel, or tin as well. Regardless of the material used, the shield should shield any part of the probe which will be in contact with the polymer to be tested.

The next step of this methodology is applying the same test signal as applied in the previous step through the sensor to a reference material, such as a fixed value resistor. This provides the quantitative character of the procedure. The reference material should have a fixed resistance to determine a reference voltage. A voltage difference between the test signal applied to the polymer at slow state transition stage and the test signal applied to the reference material as the reference voltage is then determined. This voltage difference serves as a relative indicator of the extent of chemical and/or physical change, e.g. cross-linking, present within the polymer material, based on a comparison of magnitude of the voltage difference with respect to a comparable potential range of impedance for the polymer material from its lower impedance stage at minimal cross-linking to its high impedance stage at maximum impedance for total cross-linking.

The mechanics of processing the voltage difference to get an indication of the actual extent of cross-linking may vary. The preferred technique represented in the disclosed figures involves converting the alternating voltage to direct current and inputting this direct current to a display device which gives direct readout of a value which can be correlated with the extent of cross-linking of the polymer. This direct readout comprises a DC voltage ranging from approximately 0.5 volts at low impedance to 0 at high impedance, representing a range of magnitude of at least approximately $1 \times 10^4$ Ohms. This may extend as high as $10^8$ Ohms.

The test signal is applied by generating a low frequency signal of less than 10 Hz, having a low amplitude of less than 20 volts peak to peak, and by applying this signal to the polymer in a slow state transition stage and by applying the signal to the reference resistance. In a more preferred embodiment, the low frequency signal is approximately 0.1 Hz to 5 Hz, and consists of a low amplitude of less than 10 volts peak to peak.

Figure 2:
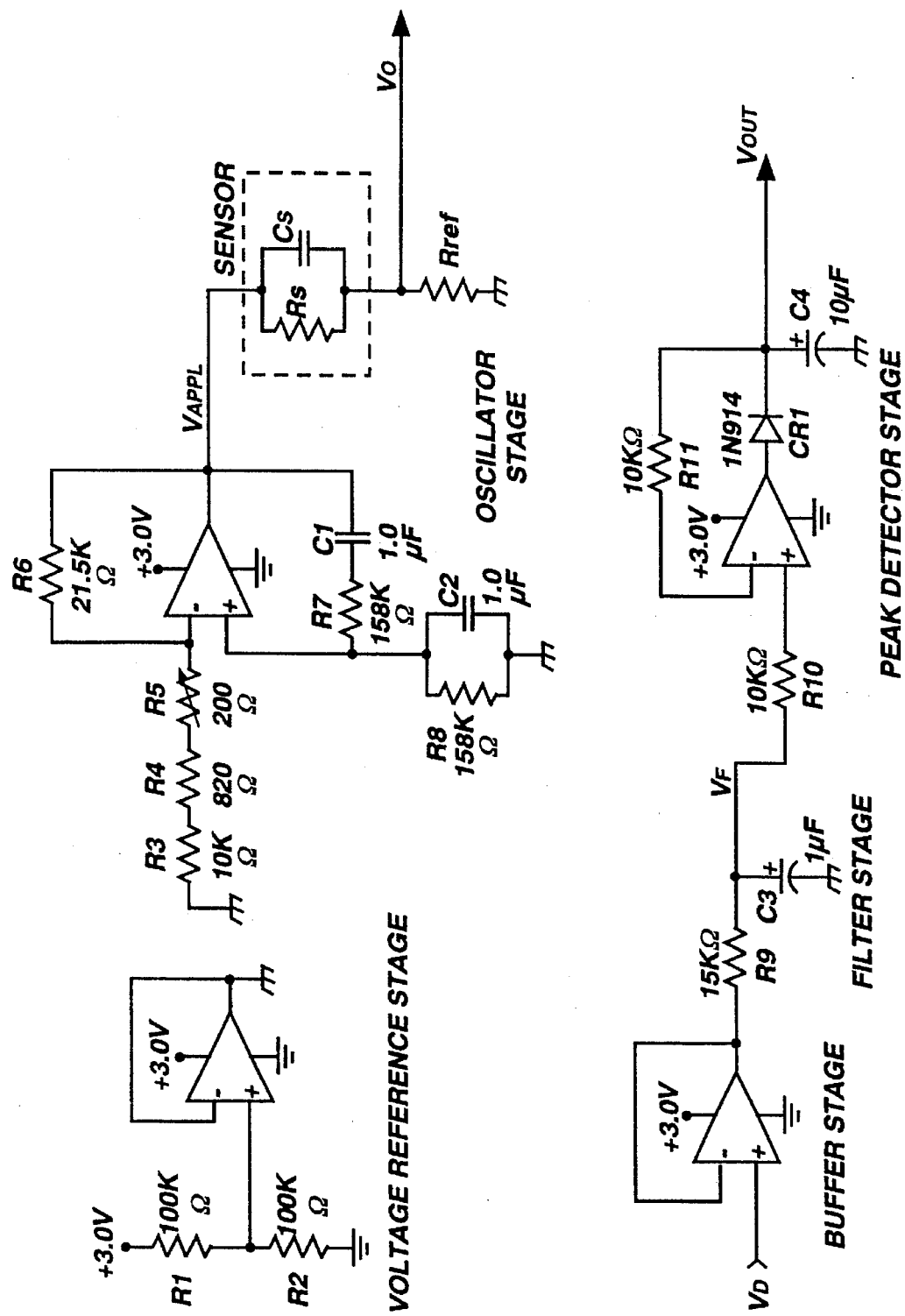
FIG. 2 shows a schematic diagram of circuitry providing a preferred embodiment of the present invention.

FIGS. 1 and 2 illustrate implementation of this invention by structuring the polymer material and the reference material within the circuit as a voltage divider wherein the voltage output is proportional to the ratio of the impedance of the reference material to total impedance of the polymer material plus the reference material. This circuit can sense a resistance change in the order of $10^4$ Ohms from the fresh stage of the material (i.e., the beginning of the slow state transition stage) to the post state transition stage. Such a range is typical for resins, plastics, paints, adhesives and caulks. In addition, the circuit can be adjusted to begin sensing in the fresh stage at anywhere from $10^3$ Ohms to $10^8$ Ohms, finishing up in the post state transition stage at anywhere from $10^7$ Ohms to $10^{13}$ Ohms.

FIG. 1 shows a block diagram in which the signal generator 20 is a sinusoidal generator which provides a 1 Hz, 1 Volt p-p signal (Vappl) which is applied to the sample sensor 21 and coated polymer to be tested. This signal is then applied to the reference resistor 22. The voltage between these function blocks $V_d$ is then buffered 24 and filtered 25, after which the resulting signal $V_f$ is converted to DC with a peak detector 26. $V_{out}$ 27 is then a DC voltage ranging from approximately 0.5 volts (for lower resistivity) up to 0 volts (for high-resistivity). The illustrated circuit can sense a range of about $1 \times 10^4$ Ohms.

Figure 3:
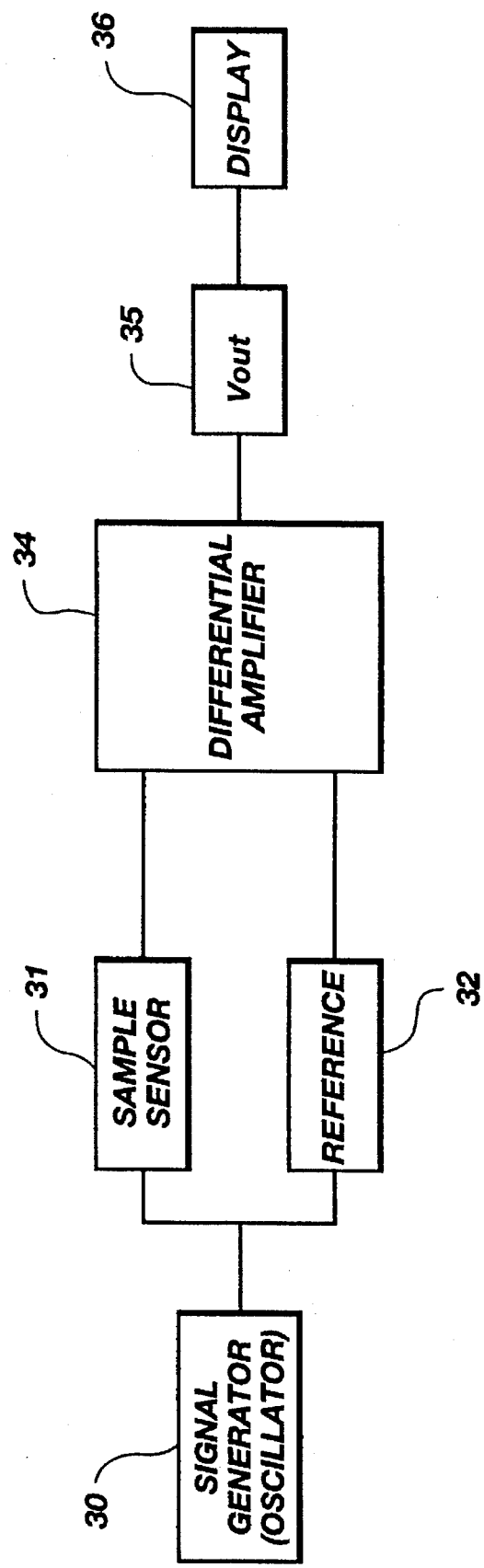
FIG. 3 shows a graphic, block diagram of an alternate embodiment of the present invention.

Referring now to FIG. 3, there is shown an alternate embodiment of the present invention. As will be appreciated by those skilled in the art, a differential amplifier could also be used to provide the voltage output which can be correlated to the extent of cross-linking. A signal generator 30 provides a signal in parallel through a sampling sensor 31 in contact with the polymer material to be tested and a reference 32 indicating a predetermined extent of cross-linking in the polymer material. Once through the sample sensor 31 and the reference 32, the signals are applied to respective first and second inputs of a differential amplifier 34. The differential amplifier 34 provides $V_{out}$ 35 indicating the difference in voltages provided from the sample sensor 31 and the reference 32. The results are indicated on a display device 36, from which the user can correlate the extent of cross-linking in the polymer material. Those skilled in the art will recognize that buffers and filters could be provided to refine the voltage out. Typically, the buffers and filters would be disposed after the differential amplifier 34.

Figure 4:
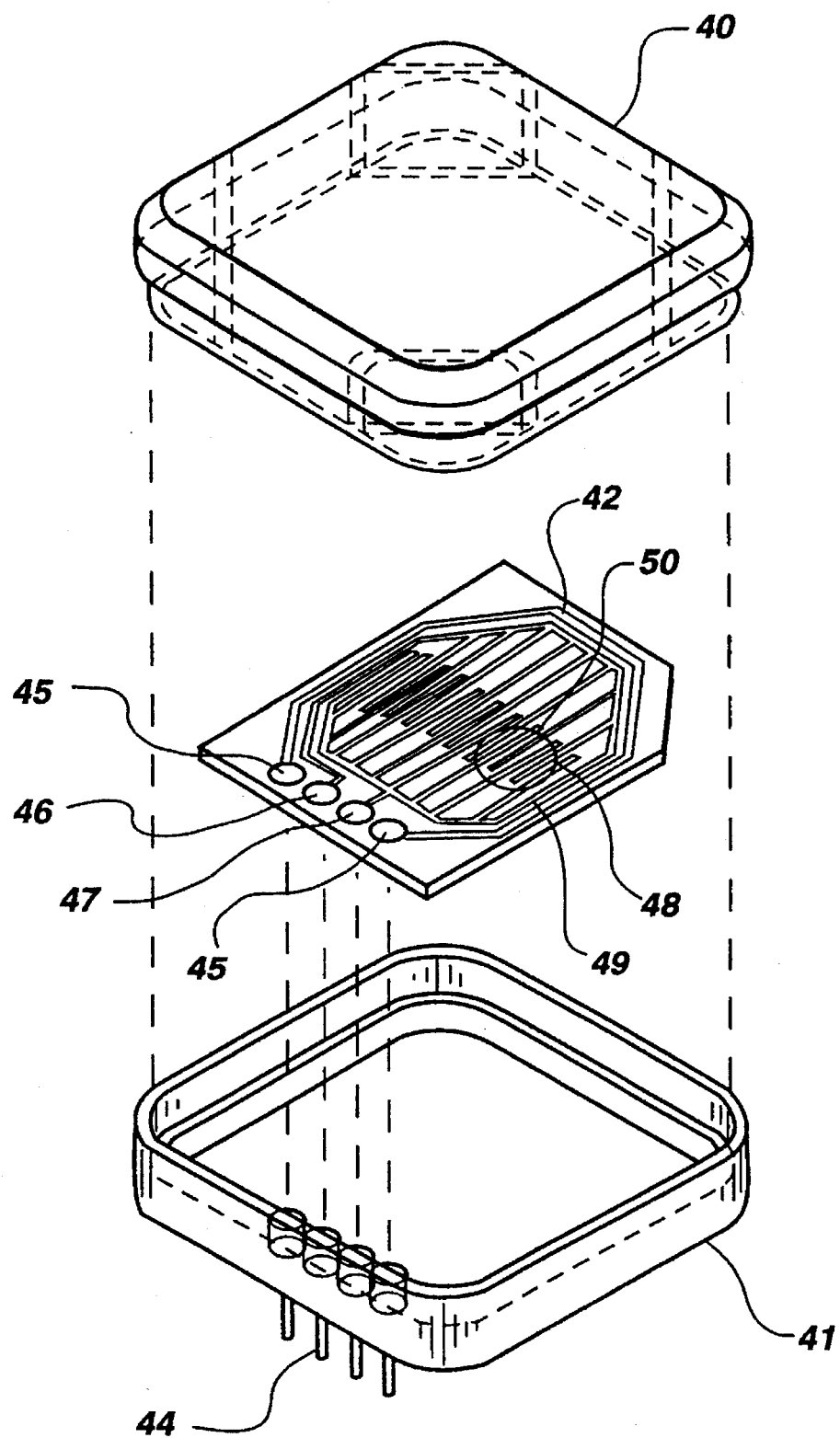
FIG. 4 shows an exploded view of a sensor device useful with the disclosed circuitry for monitoring extended chemical/physical change.

An important part of this device is the polymer-covered sensor combined with the reference. One embodiment of the sensor is shown in FIG. 4. This device comprises an upper 40 and lower 41 casement, with the interdigitated electrode sensor component 42 enclosed therein. Contact pins 44 are electrically coupled to contacts 45, 46, and 47 of the sensor component. Contacts 45 are at ground potential, while contacts 46 and 47 provide the voltage differential $V_D$ for indicating the extent of polymerization. These contacts 46 and 47 are coupled to the respective interdigitated terminal electrode 48 and 49. The actual measurement of resistivity is made by placing the polymer 50 to be tested on two or more of the adjacent terminal electrodes 48 and 49 to provide a conductance path for measuring resistance through the material. This grid of interdigitated electrodes may be etched or plated on a substrate in accordance with standard technology. The pins 44 are coupled by wires to appropriate contacts of the circuitry described in FIG. 2.

The reference 22 or 32 is typically a fixed-value resistor chosen to be approximately equal to the geometric mean of the impedance of the sensor with material in its lower resistivity state, and the same impedance as expected when the material has reached its high resistivity state. In the alternative, the reference could be any other value which represents a known extent of cross-linking. Thus, the reference could represent the maximum acceptable cross-linkage for a polymer material for a specific use. The display would indicate to the user whether that value had been surpassed. In the typical embodiment however, a proportion is given relative to the geometric mean. In this manner, the sensor and the reference can form a simple voltage divider. The output voltage from this divider is proportional to the ratio of the reference resistor to the total impedance of the sensor plus the reference resistor, as shown in Equation 1:

$$V_d \alpha \frac{R_r}{R_r + Z_s}$$

Specific considerations are relevant to FIG. 2. For example, the purpose of the voltage reference stage is simply to allow the remaining op amp stages to operate in a pseudo-dual-supply mode. This is necessary because the circuit is to be battery powered, yet generate an AC signal with no DC offset as applied to the sensor. Resistor R5 is a multi-turn trim potentiometer. It is necessary to adjust the gain of the oscillator to the point where a steady amplitude signal is produced.

The op amp chosen must have an input impedance in the area of $10^{12}$ Ohms and must operate from +3 volts. The op amp chosen for the test implementation of this invention was the Texas Instruments TSC27M4AIN. The buffer stage is necessary to prevent loading the voltage divider output voltage, $V_d$. The buffer stage raises the load impedance to about $10^{15}$ Ohms. The filter stage is an attempt to limit the bandwidth of the entire circuit and thereby reduce noise sensitivity to most stray voltages and all static electricity. For this reason, the enclosure should be carefully shielded.

When energized, the oscillator stage may not automatically start oscillating and may require a jump-start. This is accomplished by simply disconnecting R8 from the reference ground voltage, and reconnecting it. It should also be noted that $V_{out}$ will not change quickly. Therefore, when testing a new or different sensor, C4 should be momentarily shorted out, then returned to normal. This will allow $V_{out}$ to settle more quickly to its final value.

The above described structure is representative of a device for testing the extent of cross-linking of a polymer material in a pre-cure stage which is generally described to include (i) a signal generator capable of generating a low frequency, low amplitude signal; (ii) a sensor coupled to the signal generator and adapted for receiving a coating of the polymer material to be tested, the sensor having a known impedance; (iii) a reference material which has a resistivity approximately equal to an impedance of the polymer material at a known extent of cross-linking, typically the geometric mean between its lower-resistivity state, and the expected impedance of the polymer material when the polymer material has reached its high resistivity state upon full curing; and (iv) voltage means for determining the voltage difference between a signal detected through the sensor with polymer material and a signal detected through the sensor at the reference material. Converting means is coupled to the voltage means for converting the voltage difference to a factor representing the extent of cross-linking which has occurred within the polymer material. A display means may be coupled to the converting means to provide a visual readout of the extent of cross-linking in real time mode.

Figure 5:
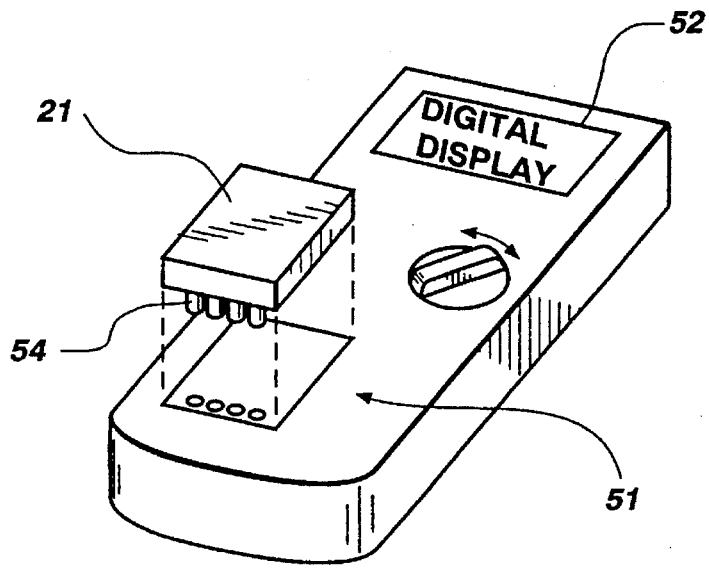
FIG. 5 shows an additional embodiment of the combined sensor and circuitry for implementing the subject invention.

The subject device can be correlated to the monitored polymer sample by numerous techniques. For example, a sample 40 of the polymer may be placed directly on the electrodes of the sensor as described in FIG. 4. This sensor can be permanently attached to the monitored polymer material so that the extent of polymerization can be checked at any time by merely inserting the pins 44 into a monitoring device 51 such as the hand held reader shown in FIG. 5. This reader 51 would contain the circuitry shown in FIG. 2, or analogous circuitry analogous to FIG. 3, including a power supply for the signal generator. The reading is then displayed on the LCD 52, giving an accurate statement of the polymer's impedance, and thus the condition of the polymer to which the sample relates. As will be explained below, this system could be readily applied with respect to batch shipments of adhesives, paints, caulks, food, dielectric fluids and numerous other materials. Once the reading is taken, the sensor 21 is returned to the material, to which it remains attached for future monitoring.

Figure 6:
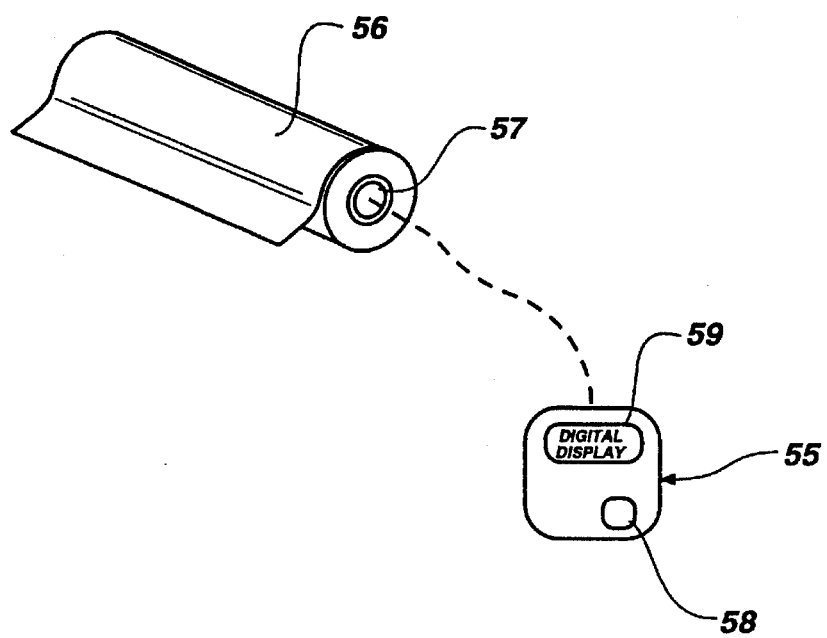
FIG. 6 discloses an additional embodiment of the subject invention, in combination with pre-preg material.

Alternately, the circuitry and sensor could be housed in a small, disposable unit such as that illustrated in FIG. 6. In this embodiment, the device 55 is a disposable unit which is coupled directly to the monitored polymer 56. Where the polymer 56 is pre-preg material, the monitoring device 55 is loaded with a sample of representative polymer associated with the pre-preg material 56. This device 55 is then permanently attached to the cardboard core 57 in visual position. When a reading is to be taken, the circuit may be activated by pressing a switch 58 which energizes the circuit and gives a reading on the LCD 59. In this manner, wherever the roll of pre-preg material is shipped, its extent of polymerization can be immediately read from the attached device 55. It will be apparent that numerous methods of permanent or temporary attachment may be envisioned. These may include sensors which have a sample of material embedded at the time of manufacture, as in FIG. 3, or may be sensors which are inserted directly into the monitored polymer.

These features also suggest the use of the present invention as part of a more general method for monitoring extent of chemical and/or physical change of a polymer material which comprises the steps of (i) identifying polymer material in slow state transition stage; (ii) attaching a sensor in contact with the identified polymer as part of the material, which sensor enables intermittent or continuous reading of the state of the polymer; and (iii) maintaining the sensor in contact with the polymer throughout the slow state transition stage of the polymer as a means for determining extent of cure of the material to which the sensor is attached. The same steps can be applied toward a batch of polymer material in slow state transition stage, wherein a sample of the polymer material is separated from the batch and the sensor is attached in contact with the sample of the identified polymer material. In this latter case, the material may be visually inaccessible, such as being in a closed container, but the sample which is attached to the outside of the container will be indicative of the contents. For this reason it is important that the sample being measured is fixed to the container so that the sample polymer experiences the same temperature and environmental conditions of the primary batch of polymer. The circuit described above could be in the form of a hand-held meter, which when attached to a sensor, would give a voltage proportional to the parameter of the material being measured.

While determining the charge carrying activity of resins and other polymer materials in slow state transition is accomplished by the above described method and device, the Inventors have discovered numerous other applications for the method and apparatus, including non polymeric materials. To demonstrate the widespread application of monitoring the slow state transition of polymeric materials and non polymeric materials, the following examples are presented.

EXAMPLE 1

Because many paints and adhesives undergo a slow state transition while in storage and while on display on a store shelf, it is important to determine whether the paint has cured to a point where it is no longer useable for its intended purpose. Initially, tests would be run on the paint or adhesive would be run to develop a curve representing cross-linking in a representative sample of the paint or adhesive. The curve would then be matched with other data about the paint or adhesive, such as the point at which cross-linking caused by slow state transition curing begins to impede performance of that particular paint or adhesive.

In order to test the paint or adhesive, a voltage would be applied to the sample sensor and to the reference. The sample sensor could require a small sample to be removed from the container, or the sample sensor could be formed integrally with the container, analogous to the embodiment shown in FIG. 6. The reference could be the geometric mean of impedance between low cross-linking and high cross-linking. In the alternative, the reference could be the extent of cross-linking at which the paint or adhesive should be discarded. Either way, the display would provide a number which the user would use to determine the extent of cross-linking in the paint or adhesive. The results of the test may indicate that the paint or adhesive has minimal cross-linking and is acceptable for continued storage; that the paint or adhesive has mid-range cross-linkage, indicating that it should be used soon, discarded, or used for a purpose which will not be hampered by higher levels of cross-linkage; or that the paint or adhesive has passed the acceptable cross-linkage threshold and should be discarded.

EXAMPLE 2

Although the device may be used to determine the cross-linking in paints and adhesives as described in Example 1, the device and method can also be used to determine the amount of suspended solvent within a polymer, such as paint. Many of today's paints rely on a solvent which keeps the polymer chains from coalescing or entangling with each other. The loss of solvent results in the polymer change of the paint reacting with one another, physically or chemically, and rendering the paint unsuitable for subsequent applications. The loss of solvent also significantly changes the charge carrying ability of the solution. In some cases the solvent is a better charge carrier than the polymer chains, and the change in charge carrying ability of the solution. Thus, by establishing a curve showing the impedance change resulting from solvent loss, a user may test a particular paint containing suspended solvents so as to determine if any loss of solvent has rendered the paint unusable for its intended purpose.

EXAMPLE 3

Unlike paints, adhesives and resins, high impedance in food products is generally good. As foods begin to spoil, i.e. sugars begin to turn to alcohol, the impedance of the food product decreases representing a change in charge carrying activity of the food product. Thus, to use impedance as a measurement of decay, a curve would first be established for that particular food product representing the impedance at different stages of decomposition. Once the impedance curve is established, repeated readings could be made by a device as described above on the same types of food and compared to a reference based on either the geometric mean of low and high impedance, or a known extent of impedance, such as the point whereat the food is no longer fit for consumption. The resulting display would indicate the extent of spoilage and, to an extent, whether the food was still safe to consume. Thus, the same type of device used to determine progressive cross-linking in polymeric materials could also be used to test for decomposition.

EXAMPLE 4

In addition to indicating spoilage in food, the change in impedance in food can also indicate the stage of dehydration in the food product. Because water is a much better conductor of electricity than is the solid food, the above described monitor could also be used to determine the extent of dehydration in foods. For example, when dehydrating fruits, it is often difficult to know when the desired level of dehydration has been obtained. However, by measuring the level of impedance the extent of dehydration may be indicated by the decrease charge carrying activity in the food product. Thus, a curve would initially be established to determine the impedance of the particular product from a fresh state to a dehydrated state. Once the curve is established, some particular point along the curve would be chosen as the reference. When sampling the product being dehydrated, the reading and the reference would be correlated to determine the extent of dehydration. Once the desired level of dehydration, ie increased impedance, is reached, dehydration may be stopped. Obviously, different values will be used for different food products.

EXAMPLE 5

The use of dielectric fluids in transformers and the like is well known in the electrical arts. A major problem with such fluids, however, is that when they fail, considerable damage is done to the transformer. Initially, dielectric fluids have a high degree of impedance, thereby impeding the flow of electricity through the fluids. However, over their useful life, the impedance decreases. Eventually, the impedance falls to such a point that electricity arcs across the fluid, causing damage to the transformer.

To prevent such occurrences, a curve could be established by taking repeated samples of dielectric fluids from a transformer to determine the changing extent of impedance of the fluid throughout its useful life. Once this is accomplished, transformers could be routinely checked to determine the extent of impedance and thus the useful life of the fluid. Once the impedance falls below a desired threshold, the fluid could be replaced. Such routine analysis would save considerable money and damage to transformers, and would also minimize the power interruptions which a blown transformer causes.

Disclosed herein is a device and method for measuring charge carrying activity in generally nonconductive materials, regardless of whether the materials are polymeric. Those skilled in the art will recognize that this disclosure is merely representative of preferred embodiments and applications of the invention and is not to be considered limiting, except as set forth in the following claims. Numerous applications and modifications of the device and method will be apparent to those skilled in the art and the accompanying claims are intended to cover such.

We claim:

1. A method for detecting an extent of chemical/physical change within a high impedance material during the shelf life of the material, said method comprising the steps of:
   a) applying a test signal through a sensor in the material during the material's shelf life to determine a level of impedance and corresponding sample voltage representative of a degree of chemical/physical change within the material;
   b) applying the same test signal through the sensor to a reference resistance having a fixed resistance to determine a reference voltage;
   c) determining a voltage difference between the test signal applied to the material during the shelf life of the material and the test signal applied to the reference resistance as the reference voltage;
   d) correlating the voltage difference as a relative indicator of the extent of chemical/physical change which has occurred within the material, based on comparison of magnitude of the voltage difference with respect to a comparable potential range of impedance for the chemical/physical change.

2. A method as defined in claim 1, said method comprising the more specific steps of:
   a) coupling the output of the test signal sent through the material of step 1a) to the input of the reference resistance of step 1b);
   b) measuring voltage at a point of coupling to create a voltage divider for determining a voltage difference between the signal applied to the material and the signal applied to the reference resistance as the reference voltage; and
   c) correlating the voltage difference as a relative indicator of the extent of chemical/physical change which has occurred within the material, based on comparison of magnitude of the voltage difference with respect to a comparable potential range of impedance for the material for its chemical/physical change.

3. A method as defined in claim 1, said method comprising the more specific steps of:
   a) coupling the output of the test signal sent through the material of step 1a) to an input of a first input of a differential amplifier;
   b) coupling the output of the test signal sent through the reference resistance of step 1b) to a second input of the differential amplifier;
   c) determining a voltage difference between the test signal applied to the material and the test signal applied to the reference resistance as the reference voltage;
   d) correlating the voltage difference as a relative indicator of the extent of chemical/physical change which has occurred within the material, based on comparison of magnitude of the voltage difference with respect to a comparable potential range of impedance for the material for its chemical/physical change.

4. A method as defined in claim 1, wherein the voltage difference is processed by converting the voltage to direct current and inputting this direct current to a display device which gives direct readout of a value which can be correlated with the extent of chemical/physical change in the material.

5. A method as defined in claim 4, wherein the direct readout comprises a DC voltage ranging from approximately 0.5 volts at low impedance to 0 volt at high impedance, representing a range of magnitude of at least approximately $1 \times 10^4$.

6. A method as defined in claim 1, wherein the test signal is applied by generating a low frequency signal of less than 10 Hz, having a low amplitude of less than 20 volts peak to peak, and by applying this signal to the material during shelf life and to the reference resistance.

7. A method as defined in claim 6, wherein the test signal is applied by generating a low frequency signal of approximately 0.1 Hz to 5 Hz, having a low amplitude of less than 10 volts peak to peak, and by applying this signal respectively to the material and the reference resistance.

8. A method as defined in claim 1, comprising the more specific step of applying the test signal to the reference resistance comprising a fixed value resistor.

9. A method as defined in claim 1, wherein the steps of applying test signal to the material and to the reference resistance comprise the specific steps of forming a voltage divider wherein the voltage output is proportional to the ratio of impedance of the reference material to total impedance of the material plus the reference resistance.

10. A method as defined in claim 1, wherein the steps comprise a process for measuring the extent of cross-linking in paint material, the method comprising the more specific step of applying paint to be tested to the sensor and processing the voltage difference in accordance with claim 1.

11. A method as defined in claim 1, wherein the steps comprise a process for measuring the extent of cross-linking in a dental polymer material, the method comprising the more specific step of applying dental polymer to be tested to the sensor and processing the voltage difference in accordance with claim 1.

12. A method as defined in claim 1, wherein the steps comprise a process for measuring the extent of chemical/physical change in food to thereby determine spoilage, the method comprising the more specific step of applying food to be tested to the sensor and processing the voltage difference in accordance with claim 1.

13. A method as defined in claim 1, wherein the steps comprise a process for measuring the extent of chemical/physical change in a dielectric fluid so as to determine the remaining useful life of the dielectric fluid, the method comprising the more specific step of applying dielectric fluid to be tested to the sensor and processing the voltage difference in accordance with claim 1.

14. A method as defined in claim 1, further comprising the step of shielding the sensor in applications to high resistivity resins with respect to static electricity.

15. A method of monitoring extent of chemical/physical change in a material during slow state transition of the material, so as to determine usability of the material for an intended use, the method comprising the steps of:
   a) selecting a material which has an uncertain extent of chemical/physical change within the material; and
   b) applying a test signal through a sensor disposed at least partially in the material to determine a level of impedance and corresponding sample voltage representative of a degree of chemical/physical change within the material;
   c) applying the same test signal through the sensor to a reference resistance having a fixed resistance to determine a reference voltage;
   d) determining a voltage difference between the test signal applied to the material prior to use and the test signal applied to the reference resistance as the reference voltage;
   e) correlating the voltage difference as a relative indicator of the extent of chemical/physical change which has occurred within the material, based on comparison of magnitude of the voltage difference with respect to a comparable potential range of impedance for the material from a lower impedance stage to a high impedance stage; and f) determining whether the extent of chemical/physical change within the material prior to use will interfere with the intended use of the material.

16. A method as defined in claim 15, said method comprising the more specific steps of:

a) coupling the output of the test signal sent through the material of step 14b) to the input of the reference resistance of step 14c);

b) measuring voltage at a point of coupling to create a voltage divider for determining a voltage difference between the signal applied to the material and signal applied to the reference resistance as the reference voltage; and c) correlating the voltage difference as a relative indicator of the extent of chemical/physical change which has occurred within the material, based on comparison of magnitude of the voltage difference with respect to a comparable potential range of impedance for the material from its lower impedance stage to its high impedance stage.

17. A method as defined in claim 15, said method comprising the more specific steps of:

a) coupling the output of the test signal sent through the material of step 14b) to an input of a first input of a differential amplifier;

b) coupling the output of the test signal sent through the reference resistance of step 14c) to a second input of the differential amplifier;

c) determining a voltage difference between the test signal applied to the material and the test signal applied to the reference resistance as the reference voltage;

d) correlating the voltage difference as a relative indicator of the extent of chemical/physical change which has occurred within the material, based on comparison of magnitude of the voltage difference with respect to a comparable potential range of impedance for the material from its lower impedance stage to its high impedance stage.

18. A method as defined in claim 15, wherein the voltage difference is processed by converting the voltage to direct current and inputting this direct current to a display device which gives direct readout of a value which can be correlated with the extent of chemical/physical change in the material.

19. A method as defined in claim 18, wherein the direct readout comprises a DC voltage ranging from approximately 0.5 volts at lower impedance to 0 at high impedance, representing a range of magnitude of at least approximately $1 \times 10^4$ Ohms.

20. A method as defined in claim 15, wherein the steps of applying test signal to the material and to the reference resistance comprises the specific steps of forming a voltage divider wherein the voltage output is proportional to the ratio of the impedance of the reference material to total impedance of the material plus the reference resistance.

21. A method as defined in claim 15, wherein the steps comprise a process for measuring the extent of chemical/physical change in food to thereby determine an extent of dehydration, the method comprising the more specific step of applying food to be tested to the sensor and processing the voltage difference in accordance with claim 14.

22. A device for testing extent of chemical/physical change in a material during the material's shelf life, said device comprising:

a signal generator capable of generating a low frequency, low amplitude signal;

a sensor coupled to the signal generator and adapted for receiving a coating of the material to be tested, said sensor having a known impedance;

a reference resistance which has a resistivity approximately equal to a predetermined impedance of a material at a predetermined point during a chemical/physical change;

voltage means for determining voltage difference between a signal detected through the sensor with the material and a signal detected through the sensor at the reference resistance; and converting means coupled to the voltage means for converting the voltage difference to a factor representing the extent of chemical/physical change which has occurred within the material during its shelf life.

23. A device as defined in claim 22, wherein the signal generator produces a signal within the range of 0.1 Hz to 5 Hz with an amplitude of less than 20 volts peak to peak.

24. A device as defined in claim 23, wherein the signal generator comprises a sinusoidal signal generator having a peak to peak voltage of no greater than 10 volts.

25. A device as defined in claim 22, wherein the reference material comprises a fixed value resistor.

26. A device as defined in claim 22, wherein the sensor with material and the reference material collectively comprise a voltage divider wherein the voltage output is proportional to the ratio of the impedance of the reference material to total impedance of the material plus the reference material.

27. A device as defined in claim 26, further comprising a buffer circuit coupled to the voltage means, said buffer circuit providing means for raising the load impedance to greater than $10^{15}$ Ohms to preventing loading the voltage divider output voltage.

28. A device as defined in claim 27, further comprising a filter stage coupled to the buffer circuit and including means to limit bandwidth reception of the device to reduce noise sensitivity.

29. A device as defined in claim 22, further comprising display means coupled to the converting means to provide a visual readout of the extent of chemical/physical change in real time mode.

30. A device as defined in claim 29, wherein said device is contained within a housing, said housing having an opening sufficiently large to enable insertion of a quantity of material material to be tested, said housing being attached to a container of the material as an indicator of extent of chemical/physical change in real time mode.

31. A device as defined in claim 30, wherein the housing and device are prepared as a disposable item to be discarded upon completion of use.

32. A device as defined in claim 29, wherein the sensor is prepared as a disposable item, said sensor including means for replaceable detachment from the device, said device being otherwise reusable except for the disposable sensor.

33. A device as defined in claim 22, further comprising shielding means coupled around the sensor and operable to shield the sensor in applications to high resistivity resins against static electricity.

* * * * *